United States Patent [19]

Andersen et al.

[11] Patent Number: 5,487,902
[45] Date of Patent: Jan. 30, 1996

[54] CHEWING GUM COMPOSITION WITH ACCELERATED, CONTROLLED RELEASE OF ACTIVE AGENTS

[75] Inventors: Carsten Andersen, Vejle; Morten Pedersen, Rådovre, both of Denmark

[73] Assignee: Fertin Laboratories Ltd. (Dansk Tyggegummi Fabrik A/S), Vejle, Denmark

[21] Appl. No.: 308,620

[22] Filed: Sep. 19, 1994

Related U.S. Application Data

[63] Continuation of Ser. No. 820,687, filed as PCT/DK90/00189, Jul. 18, 1990, abandoned.

[30] Foreign Application Priority Data

Jul. 24, 1989 [DK] Denmark ................................. 3653/89

[51] Int. Cl.⁶ ............................................ A23G 3/30
[52] U.S. Cl. .................................... 426/3; 426/4; 426/654
[58] Field of Search ....................................... 426/36, 654

[56] References Cited

U.S. PATENT DOCUMENTS

| | | |
|---|---|---|
| 4,238,475 | 12/1980 | Witzel et al. |
| 4,387,108 | 6/1983 | Koch et al. ................................. 426/4 |
| 4,493,849 | 1/1985 | Carroll et al. |
| 4,518,615 | 5/1985 | Cherukuri et al. ........................ 426/4 |
| 4,597,970 | 7/1986 | Sharma et al. ........................... 426/5 |
| 4,675,190 | 6/1987 | Glass et al. .............................. 426/5 |
| 4,983,404 | 1/1991 | Raman et al. ............................ 426/3 |

FOREIGN PATENT DOCUMENTS 78832  5/1984  Finland ............................ A61K 7/16

*Primary Examiner*—Jeanette Hunter
*Attorney, Agent, or Firm*—Donald S. Dowden

[57] ABSTRACT

A chewing gum composition with accelerated, controlled release of active agents comprising one or more active agents, a chewing gum base and optionally conventional auxiliary agents and additives. The chewing gum is prepared on the basis of a chewing gum base having a resin component containing at least 25 weight % of a particular resin. The accelerated, controlled release of the active agents is obtained by adding at least one solubilizer having an HLB of 14–20 in a quantity of 0.1–10 weight % to the chewing gum composition.

16 Claims, No Drawings

005,487,902

CHEWING GUM COMPOSITION WITH ACCELERATED, CONTROLLED RELEASE OF ACTIVE AGENTS

This is a continuation of application Ser. No. 07/820,687, filed as PCT/DK90/00189, Jul. 18, 1990, now abandoned.

TECHNICAL FIELD

The present invention relates to a chewing gum composition with accelerated controlled release of active agents comprising one or more active agents, a chewing gum base and optionally ususal auxiliary agents and additives. The invention furthermore relates to a process for the preparation of a chewing gum composition and the use of a solubilizer for accelerated controlled release of active agents in a chewing gum composition.

BACKGROUND ART

In recent years there has been great interest in finding methods of releasing active agents from chewing gum in a controlled manner. The extensive interest is both due to the wish to use chewing gum as a delivery system, for instance for drugs, and the wish to be able to release costly ingredients, such as flavours (aromas) and highly potent (or intensive) sweeteners, in moderate quantities during the relatively short chewing period.

Many factors determine the extent and speed of the release of a substance from a chewing gum. A decisive feature is the solubility of the substance. A substantially water-soluble substance is thus usually released quickly, whereas a substantially fat-soluble substance is bound more or less firmly to the water-insoluble ingredients of the chewing gum, the latter causing a slower and sometimes insufficient release during the usual chewing period.

The ratio of soluble to insoluble ingredients in the chewing gum composition, the size of the chewing gum piece, as well as the chewing intensity and the secretion of saliva of the chewer are also of importance to the release. Usually it is neither possible nor desirable to alter the latter factors.

Therefore it is necessary to involve other methods when it is desired to influence the release. In general, such methods aim at influencing the dissolution rate of the substance by coating, absorption or adsorption or by encapsulation in other materials. Hydrophilic compounds can be used for substances of a poor water-solubility as a means for achieving an improved and faster release. Examples of such substances with relatively limited solubility are for instance flavourings and relatively sparingly soluble sweeteners having a strong sweetening effect such as saccharine and aspartame, as well as many drugs.

It is a well-known problem in chewing gum preparation that only a small share of the aroma agents added are released from the chewing gum within the ususal chewing period of 2 to 10 minutes. It is not unusual that the amount of aroma agent relased stated as a percentage of the total quantity of aroma agent added, is of the following order:

After chewing for 2 minutes: 5 to 15%

After chewing for 5 minutes: 7 to 20%

After chewing for 10 minutes: 10 to 25%

Which means that a very large share, 75 to 90% of the aroma agents added is wasted when the chewing gum is thrown away. This is the reason why a relatively large quantity of aroma agents is used in chewing gum compared to other confectioneries. The aroma agents often being costly ingredients, the quantity of these in a chewing gum composition, although usually only present in a quantity of around 0.5 to 2.0%, is of great importance to the price and consequently to the competitiveness of the product.

In recent years extensive research has been carried out with respect to the use of chewing gum as a delivery system for medicines. This delivery system has proven especially suitable when a local effect in the oral cavity or the pharynx is desired or when an absorption of the medicine via the mucous membrane of the mouth is required in such cases when it is desirable to avoid the so-called "first pass" effect, that is the catabolism in the liver at the first passage, or when the medicine is sensitive to the environment in the gastrointestinal tract.

Several methods have been provided for the preparation of a chewing gum composition capable of releasing specific components in a controlled manner. Thus, a number of processes are known for obtaining an improved release of specific aroma agents and highly potent sweeteners with the purpose of prolonging the perception of taste when chewing a chewing gum.

U.S. Pat. No. 4,238,475 discloses a chewing gum comprising a water-insoluble thereapeutic component which is coated with a water-soluble coating agent to prevent resorption of the therapeutic component back into the gum base. The release of the therapeutic component is, however, conditional on the coating remaining intact during the chewing. As a result, the therapeutic component does not come into direct contact with the oral cavity and cannot therefore be used for medicines intended to be locally effective in the oral cavity and the pharynx. Furthermore, the method of preparation is elaborate and further complicated by the fact that the coating must not be destroyed during the preparation.

EP patent application No. 227,603 discloses a chewable delivery system comprising an active agent coated with lecithin, polyoxyalkylene, glyceride etc and then incorporated in a matrix system comprising among other things gelatine, water and sweetener. Also in this case the active agent passes through the oral cavity in a coated form and will therefore not produce a local effect.

EP patent application No. 229,000 discloses a process and a chewing gum for the protection and controlled release of an active agent, including medicine, highly potent sweeteners and aroma agents. The active agent is provided with a hydrophobic coating using a melt blend of polyvinyl acetate and plasticizer whereupon the blend is cooled, ground, sieved and blended with usual chewing gum ingredients. It is stated chat a delayed release in the order of 10 to 20 minutes can be obtained, but this does, however, not automatically result in an increase of the total quantity of substances released. The process is rather complicated and requires the active agent To be able to stand the temperatures involved in the process.

EP patent application No. 217,109 discloses a chewing gum in which prolonged and controlled release of, among other things, pharmaceutical agents, food ingredients and confectionery ingredients in multi-micro encapsulation hereof is obtained by means of, for instance, cellulose compounds, polyvinyl pyrrolidone, starch or saccharose etc. The process is, however, complicated and difficult to control.

U.S. Pat. Nos. 4,493,849 and 4,597,970 disclose that lecithin can be used in chewing gum to improve the mouthfeel of the chewing gum and to increase the moistening properties and texture.

U.S. Pat. No. 4,518,615 discloses a chewing gum base composition that does not adhere to dentures, removable and fixed oral prostethic devices, filings or natural teeth, said chewing gum base composition including in weight percent about 10–30% elastomer, 2–18% elastomer solvent, 15–45% polyvinyl acetate, 2,0–10% emulsifier, 0,5–15% low molecular weight polyethylene, 0,5–10% waxes, 10–40% plasticizer and 0–5% fillers.

DK patent application No. 5386/83 discloses a method for obtaining longer impact times in The oral cavity when treating fungal infections in the oral cavity. This is obtained by formulating antifungally active compounds, especially imidazole and triazole derivatives, with special gel agents such as cellulose ethers, sodium alginate and propyleneglycol alginate, in order to obtain a better adhesion of the active agent to the oral cavity. It is, however, unpleasant and difficult to keep such gelatinous preparations in the mouth for long and the impact of the active agent will vary considerably depending on how long it is kept in the mouth.

U.S. Pat. No. 4,514,382 discloses a method for solubilization of the water-insoluble antigingivitis agent, imidazolyl- 1,1-(p-chlorophenoxy)-3,3-dimethyl 2-butanone, in oral compositions. Mouth rinses, chewing gum, tooth powder and tooth paste are mentioned as oral compositions, but only the use in mouth rinses and tooth paste is documented. If, on the basis of what is stated in the above U.S. patent, a person skilled in the art attempts to prepare a chewing gum with the amounts of solubilizer stated, it will be seen for most gum bases that the chewing gum base is also solubilized, which means that the chewing gum disintegrates when chewed and is thus totally unacceptable.

Thus, there is still a need for an acceptable chewing gum composition which can deliver an active agent of relatively limited solubility to be effective locally in the oral cavity or the pharynx or to be absorbed through the mucous membrane of the mouth, while still being pleasant to take or use, whether a medical effect or a relishing effect is desired as in the cases where the active agent is for instance a medicine or an aroma agent, respectively.

Surprisingly, it has been found that it is possible to obtain a chewing gum composition with accelerated controlled release of active agents comprising one or more active agents, a particular selected chewing gum base and usual auxiliary agents and additives.

DISCLOSURE OF INVENTION

The chewing gum composition according to the invention is characterised in that the resin component of the chewing gum base contains at least 25 weight % of a resin selected among terpene resins, glycerolester of polymerised rosin, pentaerythritol ester of wood or gum rosin, pentaerythritol ester of partially hydrogenated wood or gum rosin, glycerolester of partially hydrogenated wood or gum rosin and high molecular weight polyvinyl acetate resins with a molecular weight of at least 30,000 and that at least one solubilizer in a quantity of 1–10 weight % has been added to the chewing gum composition, said solubilizer having a HLB value of 6–10 or 14–20.

Thus, according to the invention it has been found that it is possible to obtain a substantial increase in the released quantity of substances having poor water-solubility, compared to the release from conventional compositions without the use of solubilizer.

It has generally been assumed that only small quantities of surfactant can be added to chewing gum and from a theoretical point of view it would be assumed that the addition of larger quantities would usually result in extreme softening and solubilization of the entire chewing gum base portion. However, this has been found not to be the case when as chewing gum base one is selected wherein the resin portion consists of at least 25 weight % of the above particularly suitable resins. In some cases such chewing gum bases may per se contain a surfactant with a slight solubilizing effect, however usually only in small concentrations such as for instance 0–12 weight % of the gum base and ususally only from 0 to 6 weight % thereof. Such surfactants, usually in the form of emulsifiers, affect the gum base by emulsifying water thereinto. It has turned out that these emulsifiers may have a slight solubilizing effect on an active agent added to the chewing gum, but this effect is usually of small extent compared to the solubilizing effect obtained by the solubilizers suggested according to the invention. The quantities of solubilizers stated in the present specification and claims do not comprise such optional surfactants conventionally already contained in the chewing gum base used as starting material.

According to the invention it has been found that it is possible without heating by simply admixing a solubilizer, optionally by simple pre-mixing, to obtain an improved release of active agents without an unacceptable softening of the chewing gum taking place when said chewing gum base is used.

It has been found that the solubilizer quantity is decisive of the extent of the release of a predetermined active agent. In the case of active agents which are released to a smaller extent without the use of solubilizer (for instance 10–40 weight % after 10 minutes of chewing) it will often be necessary to add more than 1 weight % solubilizer to obtain a positive effect. In the case of active agents which have a very poor release without solubilizers being added (for instance a few weight % after 10 minutes of chewing) a considerable increase in the release will be observed by merely adding 1 weight % solubilizer. The upper limit to the addition of solubilizers depends on the chewing gum formulation, the type of gum base, the type of active agent and the quantity thereof and not least the type of solubilizer. Usually it will not be possible to add more than 30 weight % solubilizer without the consistency of the chewing gum becoming totally unacceptable, and often such large quantities are not necessary or desirable as these often will result in a too rapid release. The selection of the type of solubilizer used and the quantity thereof will thus always depend on the type and quantity of the active agent and of the chewing gum formulation in question. Tests have shown that a good release is obtained with a solubilizer concentration of 1–10 weight %, preferably 3–6 weight % without the consistency thereby being unacceptable.

It is a further advantage of the invention that the solubilizer used is generally an inexpensive ingredient, which does not noticeably affect the price of the chewing gum composition in the concentrations used, and that it does not require the procurement of expensive special apparatus.

It is an additional advantage of the chewing gum composition according to the invention that it is now possible to prepare products with a new taste profile and/or effects, as active agents are released which, because of their poor rate of release, it was not economically sound to use before, or not possible at all and because they can be released in other proportions.

Furthermore, several solubilizers have already been approved for use in food articles or accepted for use in medicines.

It is known that by placing active agents in the dragée layer of a chewing gum a faster and larger release can be obtained than the one obtained by a conventional incorporation of the active agent into the core of the chewing gum. However, experience shows that the use of this principle means that although a larger portion of the active agent is released a large portion of said active agent is quickly resorbed by the gum base in the beginning of the chewing period whereby on the whole only a relatively small advantage in the form or a larger release during the first minute of the chewing is obtained. With a chewing gum composition according to the invention it is, on the other hand, possible to obtain a considerably more complete relase over a longer chewing period, and it is also technically easier to incorporate the active agent in the core of the chewing gum itself compared with the incorporation in the dragée layer.

The further scope of the applicability of the invention will become apparent from the detailed description given below. However, it should be understood that the detailed description and specific examples, while indicating preferred embodiments of the invention, are given by way of illustration only, since various changes and modifications within the spririt and scope of the invention will become apparent to those skilled in the art from this detailed description.

A particular embodiment of the chewing gum composition is characterised in that the resin component of the chewing gum base contains at least 40% of a resin selected among terpene resins, glycerol ester of polymerised rosin, pentaerythritol ester of wood or gum rosin, pentaerythritol ester of partially hydrogenated wood or gum rosin, glycerolester of partially hydrogenated wood or gum rosin and high molecular weight polyvinyl acetate resins with a molecular weight of at least 30,000.

In a further advantageous embodiment the chewing gum composition is characterised in that the resin component of the chewing gum base contains a terpene resin of natural or synthetic origin.

In principle, all types of surfactants which do not display an unacceptable toxicity in the concentration used can be used as solubilizer. As an example of types of surfactants to be used as solubilizer in a chewing gum composition according to the invention reference is made to H. P. Fiedler, Lexikon der Hilfstoffe für Pharmacie, Kosmetik und Angrenzende Gebiete, page 63–64 (1981) and the lists of approved food emulsifiers of the individual countries.

Both anionic, cationic, amphoteric and nonionic solubilizers can be used, but usually the solubilizer used is either anionic or nonionic as mainly such solubilizers are approvable for use in food or medicines. In cases where the active agent is reactive it is usually an advantage to use a nonionic solubilizer as such are not very reactive and therefore do not affect the stability of the active agent unfavourably.

When selecting a solubilizer, the fact that such solubilizer must have an acceptable taste must also be taken into account. Therefore it will be natural to find the suitable substances among approvable food emulsifiers and emulsifiers acceptable for use in medicines for oral administration.

Suitable solubilizers include polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids, which solubilizers are all known for use as food emulsifiers, and polyoxyethylated hydrogenated castor oil (for instance such sold under the trade name CREMOPHOR), blockcopolymers of ethylene oxide and propylene oxide (for instance as sold under the trade name PLURONIC or the trade name POLOXAMER), polyoxyethylene fatty alcohol ethers, polyoxyethylene sorbitan fatty acid esters, sorbitan esters of fatty acids and polyoxyethylene steraric acid ester, all known in the EEC for use as pharmaceutical-cosmetical emulsifiers.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, blockcopolymers of ethylene oxide and propyleneoxide and polyoxyethylene fatty alcohol ether. The solubilizer may either be a single compound or a combination of several compounds. The expression "solubilizer" is used in the present text to describe both possibilities, the solubilizer used must be suitable for use in food and/or medicines.

It has been found that there may be a connection between the solubility profile of the active agent and the HLB value of the solubilizer used. However, it has not been possible to establish a correlation between the solubility parameters of the active agent and the HLB value of the solubilizer. In practice, it has been found that generally a good effect is obtained by using a solubilizer with a HLB value in the range from 14 to 20, preferably 14–18. However, good effects have also been found with solubilizers with HLB values in the range from 6 to 10, preferably 7–8. The HLB values used in the present specification and claims are taken from the literature or based on information by the supplier. As to the determination of HLB values and examples of HLB values for different solubilizers, reference can be made to the above mentioned H. P. Fiedler, Lexikon der Hilfstoffe for Pharmacie, Kosmetik und angrenzende Gebiete, page 65–69, 1981.

The gum base used in the chewing gum according to the invention is generally prepared in a conventional manner by heating and mixing the different ingredients such as elastomers, resins, inorganic fillers, waxes, fats and emulsifiers etc.

Any of the usual elastomers can be used in a quantity of typically 3–25 weight %. The elastomer may be of natural origin, for instance such as stated in Food and Drug Administration, CFR, Title 21,Section 172.615 , as "Masticatory Substances of Natural Vegetable Origin", or synthetic elastomers, such as styrene butadiene gum (SBR), butyl gum (isobutylene isoprene copolymer), or polyisobutylene (as stated in the above section of FDA under Masticatory Substances, Synthetic).

The inorganic fillers that form part of the chewing gum base may be present in a quantity of up to 50 weight %, preferably 0–30 weight %. Calcium carbonate, talc, sodium sulfate, aluminium oxide, magnesium carbonate, kaolin, silicium oxide and calcium phosphates alone or in a mixture of more thereof may be mentioned as suitable fillers. Waxes and fats are conventionally used for the adjustment of the consistency and softening of the chewing gum base when preparing chewing gum bases. In connection with the present invention any conventionally used and suitable type of wax may be used, such as for instance rice bran wax, polyethylene wax, petroleum wax (refined paraffin and microcrystalline wax), paraffin, bee wax, carnauba wax, candelilla wax, cocoa butter, degreased cocoa powder and any suitable oil or fat, as for instance completely or partially hydrogenated vegetable oils or completely or partially hydrogenated animal fats. The quantity of wax used may be in the range from 0–50 weight %.

To soften the gum base further and to provide it with water binding properties, which gives the gum bases a pleasant smooth surface and reduces its adhesive properties, one or more emulsifiers may usually be added. Mono and diglycerides of edible fatty acids, lactic acid esters and acetic acid esters of mono and diglycerides of edible fatty acids, sugar esters of edible fatty acids, Na-, K-, Mg- and Ca-stearates, lecithin, hydroxylated lecithin and the like may be mentioned as examples of legal and conventionally used emulsifiers added to the chewing gum base.

As mentioned earlier, said emulsifiers, which are conventionally used in quantities of 0–12 weight %, preferably 0–6 weight % of the gum base, may have a solubilizing effect on the active agent, later added to a chewing gum prepared on the basis of such emulsifier containing chewing gum base. However, this effect is usually of a small extent compared to the effect of the solubilizers which in practice of the present invention usually are added during the preparation of the chewing gum and not to the chewing gum base.

Furthermore, the chewing gum base may contain the usual additives, such as antioxidants, for instance BHT, BHA, propylgallate and tocopherols as well as preservatives and colourants.

Resins should also be mentioned as a further component forming part of a chewing gum base, said resins being necessary to obtain the right chewing consistency and as solubilizer for the elastomers of the chewing gum base.

As mentioned above, the resin used is of importance to the chewing gum composition according to the invention. It has thus been found that not all conventionally used resins are useable in a chewing gum base to be used in a chewing gum also containing a solubilizer.

Thus the addition of a solubilizer, even in small quantities of for instance from 0.5 weight %, often results in the chewing gum obtaining an unacceptable consistency by either turning unusually soft or, what is usually the case, totally disentegrating within the first few minutes of the chewing period.

However, it has been found that this can be avoided if at least 25% of the total resin quantity is comprised by one or more of the following essential resins: natural or synthetic terpene resins (as for instance the α- and β-pinene, dipentene or delta-limonene), glycerol ester of polymerised rosin, pentaerythritol ester of wood or gum rosin, pentaerythritol ester or glycerol ester of partially hydrogenated wood or gum rosin or high molecular weight polyvinyl acetate resins with a molecular weight exceeding 30,000.

As mentioned, said essential resins must constitute at least 25%, especially 40%, of the total gum base resin to provide the gum base with acceptable properties. The gum base may contain one of the essential resins or a mixture of two or more of the essential resins.

Apart from the above condition that at least 25 weight % of the essential resins mentioned must be present, any of the conventionally used resins may be used in the gum base, that is also glycerol ester of wood or gum rosin, glycerol ester of partially dimerised rosin, methyl ester of partially hydrogenated rosin and low molecular weight polyvinyl acetate, that is with a molecular weight below 30,000.

It is of course obvious to a person skilled in the art that the precise necessary minimum quantity of the essential resins may depend on many different circumstances of the formulation of both the chewing gum base and the chewing gum.

For instance, the use of mainly low molecular weight elastomers and a high content of softeners, fats and waxes will often make it necessary to use a larger quantity of essential resins to obtain a satisfactory cohesive piece of chewing gum.

Yet another embodiment of the composition according to the invention is characterised in that it furthermore contains up to 60 weight % of at least one carrier, which carrier(s) forming a solid dispersion together with the active agent.

The carrier used to form the solid dispersion may be selected among all the substances which have proved useable for this purpose, for instance polyethylene glycols, urea, polyvinyl pyrrolidone, sweeteners, such as sorbitol, xylitol, mannitol, sugar and dextrose, citric and succinic acids, bile acid and derivatives thereof, steroles and the like, surfactants, pentaerythritol and corresponding globular compounds, polymers as well as urethane, fatty acid compounds, such as glyceryl oleate, cyclodextrines, ascorbic acid, acetamide, nicotinic acid, succinamide, sodium citrate, dextranes, methylcellulose, sodium alginate, gelatine, carrageenan, pectin, sodium carboxy methylcellulose, polyvinyl alcohol, gum arabic, tragacanth, guar gum, and any combination of said substances, preferably polyethylene glycol or polyvinyl pyrrolidone, particularly preferable polyethylene glycol 1000–20,000, especially polyethylene glycol 6,000. A single carrier, or when suitable, more carriers in combination may be used. The expression "carrier" is used in the present text to describe both possibilities.

The method of preparing the solid dispersion may be selected among all the methods which have proved useable for this purpose. The active agent and the carrier may for instance be melted together and then cooled momentarily. The mixture is then ground and sieved to a suitable particle size. Alternatively, the active agent and the carrier is dissolved in a liquid which is evaporated to form a coprecipitation of the active agent and carrier, said coprectpitation optionally being ground and sieved. Of these methods the former, also called-the melting method, is often preferred, as the solvents used for the latter method are often hazardous to the health and therefore avoided.

The invention has proved advantageous for controlled, accelerated release of active agents selected among the group dietary supplements, oral and dental compositions, antiseptic agents, pH adjusting agents, anti-smoking agents, sweeteners, flavourings, aroma agents or drugs, such as for instance paracetamol, benzocaine, cinnarizine, menthol, carvone, coffeine, chlorhexidine-di-acetate, cyclizine hydrochloride, 1,8-cineol, nandrolone, miconazole, mystatine, aspartame, sodium fluoride, nicotine, saccharin, cetylpyridinium chloride, other quaternary ammoniumcompounds, vitamin E, vitamin A, vitamin D, glibenclamide or derivatives thereof, progesterone, acetylsalicylic acid, dimenhydrinate, cyclizine, metronidazole, sodium hydrogencarbonate, the active components from ginkgo, the active components from propoils, the active components from ginseng, methadone, oil of peppermint, salicylamide, hydrocortisone or astemizole.

The active agents to be used in connection with the present invention may be any substance desired to be released from the chewing gum. The active agents for which an accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavourings etc.

Examples of active agents in the form of dietary supplements are for instance salts and compounds having the nutritive effect of vitamin $B_2$ (riboflavin), $B_{12}$, folinic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutrients acccepted by the authorities in different countries such as for instance US code of Federal Regulations, Title 21, Section 182.5013.182 5997 and 182.8013–182.8997.

Examples of active agents in the form of compounds for the care or treatment of the oral cavity and the teeth, are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, page 547–578; metal salts, complexes and compounds with limited water-solubility, such as aluminium salts, (for instance aluminium potassium sulfate $AlK(SO_4)_2$, 12 $H_2O$) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, aminofluorides, stannous fluoride), phosphates, carbonates and selenium.

Cf. furthermore J. Dent.Res. Vol. 28 No. 2, page 160–171, 1949, wherein a wide range of tested compounds are mentioned.

Examples of active agents in the form of agents adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Examples of active agents in the form of sweeteners include for instance the so-called highly potent sweeteners, such as for instance saccharin, cyclamate, aspartame, thaumatin, dihydrocalcones, stevioside, glycyrrhizin or salts or compounds thereof.

Further examples of active agents are for instance aroma agents of any type as well as medicines of any type.

Examples of active agents in the form of medicines include coffeine, salicylic acid, saltcyl amide and related substances (acetylsalicylic acid, choline saltcylate, magnesium saltcylate, sodium salicylate), paracetamol, salts of pentazocine (pentatocine hydrochloride and pentazocinelactate), buprenorphine hydrochloride, codeinc hydrochloride and codeinc phosphate, morphine and morphine salts (hydrochloride, sulfate, tartrate), methadone hydrochloride, ketobemidone and salts of ketobemidone (hydrochloride), β-blockers, (propranolol), calcium antagonists, verapamil hydrochloride, nifedinpine as well as suitable substances and salts thereof mentioned in Pharm. Int., Nov. 85, pages 267–271, Barney H. Hunter and Robert L. Talbert), nitroglycerine, erythrityl tetranitrate, strychnine and salts thereof, lidocatne, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopresstn acetate (DDAVP), isoxsuprine hydrochloride, ergotamine compounds, chloroquine (phosphate, sulfate), isosorbide, demoxytocin, heparin.

A further particularly preferred preparation according to the invention comprises up to 50 weight %, preferably 0.1–10 weight % active agent in the form of a solid dispersion hereof in a carrier, up to 60 weight %, preferably approximately 20 weight % of the carrier used to obtain the solid dispersion, 1–10 weight % solubilizer, 15–80 weight %, preferably approximately 35 weight % chewing gum base and up to 85 weight %, preferably approximately 35 weight % auxiliary substances and additives.

A particularly preferred preparation according invention comprises up to 50 weight %. preferably 0.1–10 weight % active agent admixed with at least one solubilzer, 15–80 weight %, preferably approximately 35 weight % chewing gum base, up to 85 weight %, preferably approximately 50–60 weight % auxiliary agents and additives and 1–10 weight %, preferably approximately 5 weight % solubilizer.

The invention further relates to a process for the preparation of a chewing gum composition according to the invention by preparing a chewing gum base on the basis of conventional chewing gum base ingredients and then in a conventional manner preparing a chewing gum composition while adding one or more active agents and additives and optionally usual auxiliary agents, characterised by using a chewing gum base wherein the resin portion consists of at least 25 weight % of a resin selected among terpene resins, glycerol ester of polymerised rosin, pentaerythritol ester of polymerised rosin, pentaerythritol ester of wood or gum rosin, pentaerythritol ester of partially hydrogenated wood or gum rosin, glycerol ester of partially hydrogenated wood or gum rosin and high molecular weight polyvinyl acetate resins with a molecular weight of at least 30,000, and adding 1–10 weight % of at least one solubilizer, said solubilizer having a HLB value of 6–10 or 14–20.

A particular embodiment according to the invention is characterised in that the active agent is intimately mixed with the solubilizer, optionally during heating, before adding to the chewing gum composition.

If a carrier is used, the process may advantageously be carried out by forming a solid dispersion of the active agent in a carrier prior to mixing the active agent with the solubilizer.

The invention furthermore relates to the use of a solubilizer for accelerated controlled release of active agents in a chewing gum composition. By such use it is possible to obtain an increase in the rate of release and thereby an increase in the total quantity released during a given chewing period.

As auxiliary agents and additives selected for use in the inventive chewing gum composition any auxiliary agents and additives for the conventional use in chewing gum may be used. Examples thereof are sweeteners, aroma agents, colourants and softening and consistency adjusting agents Sweeteners usable for the chewing gum composition include for instance sorbitol, xylitol, mannitol, palatinit, malbit, lactitol, hydrogenated glucose syrup, saccharose, glucose syrup, fructose, dextrose, lactose, sorbose and intensive natural or synthetic sweeteners, such as saccharin, cyclamate, aspartame, acesulfame K, thaumatin, glycyrrhizin, dihydrochalcones and salts and derivatives hereof. The choice of sweetener or sweeteners will partly depend on whether a sugar-free product is required or not, partly on which consistency and sweetness are required in the composition according to the invention.

It is possible to use smaller quantities of many of the conventionally used highly potent sweeteners because of their increased release.

The aroma agents usable for the chewing gum composition are for instance natural and synthetic flavourings (including nature identical flavourings) in the form of essential oils, essences, extracts, powders, including acids and other substances capable of affecting the taste profile.

Examples of liquid and powdered flavourings include coconut, coffee, chocolate, vanilla, grape fruit, menthol, liquorice, anise, apricot, caramel aroma, honey aroma, pineapple, strawberry, raspberry, tropical fruits, cherries, cinnamon, peppermint, wintergreen, spearmint, eucalyptus and mint. As mentioned above, the aroma agent may in many cases be used in quantities smaller than those conventionally used.

There are no special requirements to the colourants, which may be of natural or synthetic origin, except that they must be approvable for use in food and medicines.

Glycerol, propylene glycol, lecithin, triacetin, hydrogenated glucose syrup, sorbitol 70%, glucose syrup, waxes and oils can be mentioned as suitable softeners or consistency adjusting agents for use in the composition according to the invention. As a result, the product is provided with a consistency pleasant for chewing during the desired chewing period.

The formulation of the chewing gum base depends on the type of chewing gum desired as described above or the required type of structure. Suitable raw materials for the gum base comprise substances according to U.S. Chewing Gum Base Regulations—Code of Federal Regulations, Title 21, Section 172.615.

It is a particular advantage of the invention that the chewing gum composition can be prepared using conventional ingredients, conventional equipment and conventional methods of preparation.

When the active agent has been incorporated in the chewing gum vehicle, this product may be of any known type, such as bits, optionally provided with a dragée, and sticks or chewing gum of any other desired form. The chewing gum pieces may be coated with a type of wax, a film coating or a conventional so-called candy coat based on sugar-containing or sugar free substances.

A single piece of chewing gum usually weighs between 0.4 and 20.0 g. The following Table indicates the preferred intervals for the different product types:

| Chewing gum bits | 500–3,500 mg |
| Coated chewing gum | 600–6,000 mg |
| Chewing gum sticks | 1,000–5,000 mg |

When the individual ingredients forming part of a chewing gum composition according to the invention are mentioned in singular, such mention also comprises a combination of several such ingredients, apart from instances where one particular ingredient is mentioned.

BEST MODE FOR CARRYING OUT THE INVENTION

The invention is illustrated in more details below by means of the Examples, which are not limitative of the present invention.

EXAMPLES

General Methods

Preparation of Chewing Gum Base

A chewing gum base is prepared on the basis of the following ingredients:

| | |
|---|---|
| Elastomers | 4 weight % |
| Terpene resin | 28 weight % |
| Low molecular weight PVA | 29 weight % |
| Emulsifier | 8 weight % |
| Waxes | 31 weight % |

The elastomer is ground in a conventional mixer for the preparation of chewing gum and gum base while being heated to 110°–130° C. and terpene resin and low molecular weight PVA are added slowly in small portions. Finally waxes and emulsifier are added. To ensure a homogenous base it is important that all the ingredients are added in small portions and that the subsequent portions are not added until the preceding portion is ground.

It has been found that the resulting chewing gum base does not disintegrate when the solubilizer is added.

Preparation of Chewing Gum

The chewing gum prepared in the examples have been formulated on the basis of the following basic formulation:

| Basic Formulation 1 | |
|---|---|
| Gum base | 35 weight % |
| Sorbitol powder | 10 weight % |
| Hydrogenated glucose syrup | 10 weight % |
| Active agent | 0.01–30 weight % |
| Solubilizer | 1–10 weight % |
| Optional flavour | 1.9 % |
| Optional additional sorbitol powder q.s. | 100 weight % |

The chewing gum pieces are prepared in the manner conventional for the preparation of chewing gum and using a conventional apparatus for the preparation of chewing gum.

The chewing gum base is melted or ground in a conventional chewing gum mixer. When the chewing gum base is homogenous, the other ingredients are admixed one by one in the order mentioned. Solubilizer and active agent may be admixed separately or in the form of a premixture or in a solution. Depending on the state of the ingredients and their melting point, such premixture may be a simple mixture of two or more powders, a mixture of one or more powders in one or more liquids or a mixture of more liquids at ordinary, increased or lower temperature. To ensure a good dispersion of the ingredients it may, especially when adding very small quantities of one or more of the components of the premixture, be an advantage to add these as a liquid mixture or a solution where this is possible.

It is also possible to premix or dissolve the active agent and the solubilizer into other ingredients of the formulation, for instance hydrogenated glucose syrup, flavourings, sorbitol or into the gum base itself, if deemed suitable.

Apart from admixing the gum base first, the order of the admixture is not critical. However, the mixing time after the admixture of the active agent and solubilizer should be of a duration long enough to ensure a sufficiently good dispersion of these ingredients in the chewing gum mass. Optionally supplementary flavourings are usually added lastly followed by mixing for 2 to 3 minutes.

Upon completion of the mixing, the homogenous chewing gum mass is removed from the mixer and cut out and left to cool in small pieces or is extruded to a thin sheet which is led through a cooling apparatus. The cooled mass is then extruded to a thin sheet, which is rolled on a conventional chewing gum rolling system and cut into bits of appropriate form and size.

The bits are left to harden for two to five days and are then separated by tumbling in a conventional dragée pan. Subsequently, the bits are completed by applying a thin polishing layer by film coating or a dragée coating is provided.

The release of the active agent in Examples 1–143 are determined either in vitro or in vivo.

In vitro

The tests in vitro are carried out on a chewing machine (L. Christrup et al., Arch. Pharm. Chem. Sci., 1986, 14, pages 30–36) by chewing one piece of chewing gum with a weight of 820 mg for 30 minutes in a phosphate buffer with a pH of 7.4. The results stated in the Tables are the relative release of the active agent, the release without solubilizer having been set at 100%.

In vivo

The test in vivo are all carried out by letting a person chew the chewing gum for 2, 5 and 10 minutes, repectively, whereupon the remaining content of the active agent in the chewed bit is analyzed in order to determine the quantity released.

At the tests in vivo the results also indicate relative release, the release without solubilizer having been set at 100%.

Example 1–12

The use of monoglyceride diacetyl tartaric acid ester, PANODAN 165 from Grindsted Products A/S, Denmark, as solubilizer, HLB 7, was tested in vitro in the manner described above. The results appear from Table 1.

TABLE 1

| Exampl. No. | PANODAN 165 weight % | Active agent | Content % | Relative Release | | |
|---|---|---|---|---|---|---|
| | | | | 2 min. | 10 min. | 30 min. |
| 1 | 5 | NYSTATIN | 6.25 | 2600 | 12000 | 7400 |
| 2 | 3 | NYSTATIN | 6.25 | 360 | 3100 | 2000 |
| 3 | 1 | NYSTATIN | 6.25 | 80 | 170 | 240 |
| 4 | 0 | NYSTATIN | 6.25 | 100 | 100 | 100 |
| 5 | 5 | MICONAZOLE | 6.25 | U | 54000 | 3600 |
| 6 | 3 | MICONAZOLE | 6.25 | U | 31000 | 2000 |
| 7 | 1 | MICONAZOLE | 6.25 | U | 8700 | 400 |
| 8 | 0 | MICONAZOLE | 6.25 | 100 | 100 | 100 |
| 9 | 5 | NANDROLONE | 0.625 | 100 | 267 | 245 |
| 10 | 0 | NANDROLONE | 0.625 | 100 | 100 | 100 |
| 11 | 5 | BENZOCAINE | 12.5 | 708 | 452 | 100 |
| 12 | 0 | BENZOCAINE | 12.5 | 100 | 100 | 100 |

U = infinite

In Examples 1 to 143 below chewing gum bits with a weight of 800 mg are cut out and coated with a thin layer of sorbitol with a little flavouring added. The chewing gum bits now weigh 820 mg each.

Examples 13–28

PANODAN 165 was tested in vivo in chewing gum compositions in the manner described above. The results appear from Table 2.

TABLE 2

| Example No. | PANODAN 165 weight % | Active agent | Content % | Relative Release | | |
|---|---|---|---|---|---|---|
| | | | | 2 min. | 5 min. | 10.min |
| 13 | 5 | PARACETAMOL | 10 | 163 | 144 | 152 |
| 14 | 0 | PARACETAMOL | 10 | 100 | 100 | 100 |
| 15 | 5 | MENTHOL | 1.3 | 37 | 100 | 123 |
| 16 | 0 | MENTHOL | 1.3 | 100 | 100 | 100 |

TABLE 2-continued

| Example No. | PANODAN 165 weight % | Active agent | Content % | Relative Release | | |
|---|---|---|---|---|---|---|
| | | | | 2 min. | 5 min. | 10.min |
| 17 | 5 | 1.8 CINEOL | 1.0 | — | 10 | 178 |
| 18 | 0 | 1.8 CINEOL | 1.0 | 100 | 100 | 100 |
| 19 | 5 | ANETHOL | 0.2 | 16 | — | 109 |
| 20 | 0 | ANETHOL | 0.2 | 100 | 100 | 100 |
| 21 | 5 | CARVONE | 0.5 | 135 | 201 | 202 |
| 22 | 0 | CARVONE | 0.5 | 100 | 100 | 100 |
| 23 | 5 | CINNARIZIN | 0.625 | U | U | U |
| 24 | 0 | CINNARIZIN | 0.625 | 100 | 100 | 100 |
| 25 | 5 | CYCLIZINE, Hcl | 6.25 | 420 | 179 | 53 |
| 26 | 0 | CYCLIZINE, Hcl | 6.25 | 100 | 100 | 100 |
| 27 | 5 | COFFEINE | 4.4 | 233 | 157 | 137 |
| 28 | 0 | COFFEINE | 4.4 | 100 | 100 | 100 |

Examples 29-31

The use of monoglyceride lactic acid ester, LACTODAN B30 from Grindsted Products A/S, as solubilizer, HLB 8.2, was tested in vitro in the manner described above. The results appear from Table 3.

TABLE 3

| Exampl. No. | LACTODAN B30 weight % | Active agent | Content % | Relative Release | | |
|---|---|---|---|---|---|---|
| | | | | 2 min. | 10 min. | 30 min. |
| 29 | 5 | NYSTATIN | 6.25 | 113 | 210 | 560 |
| 30 | 2 | NYSTATIN | 6.25 | 40 | 106 | 200 |
| 31 | 0 | NYSTATIN | 6.25 | 100 | 100 | 100 |

Examples 32-37

LACTODAN B30 was tested in vivo in-chewing gum compositions in the manner described above. The results appear from Table 4.

TABLE 4

| Exampl. No. | LACTO-DAN B30 weight % | Active agent | Content % | Relative Release | | |
|---|---|---|---|---|---|---|
| | | | | 2 min. | 5 min. | 10 min |
| 32 | 5 | CHLORHEXID. DI. AC | 0.625 | 155 | 108 | 103 |
| 33 | 0 | CHLORHEXID. DI.AC | 0.625 | 100 | 100 | 100 |
| 34 | 5 | PARACETAMOL | 10 | 4120 | 178 | 108 |
| 35 | 0 | PARACETAMOL | 10 | 100 | 100 | 100 |
| 36 | 5 | MENTHOL | 1.3 | 100 | 156 | 120 |
| 37 | 0 | MENTHOL | 1.3 | 100 | 100 | 100 |

Examples 38-47

The use of polyoxyethylene sorbitan fatty acid ester, TWEEN 60, HLB 14.9, as solubilizer was tested in vitro in the manner described above. The results appear from Table 7.

TABLE 7

| Example No. | TWEEN 60 weight % | Active agent | Content % | Relative Release | | |
|---|---|---|---|---|---|---|
| | | | | 2 min. | 10 min. | 30.min. |
| 38 | 5 | NYSTATIN | 6.25 | 4350 | 8400 | 5320 |
| 39 | 3 | NYSTATIN | 6.25 | 2100 | 6900 | 4600 |
| 40 | 1 | NYSTATIN | 6.25 | 180 | 1000 | 1000 |
| 41 | 0 | NYSTATIN | 6.25 | 100 | 100 | 100 |
| 42 | 5 | MICONAZOLE | 6.25 | U | 100000 | 5000 |
| 43 | 3 | MICONAZOLE | 6.25 | U | 65000 | 3300 |
| 44 | 1 | MICONAZOLE | 6.25 | U | 7800 | 590 |
| 45 | 0 | MICONAZOLE | 6.25 | 100 | 100 | 100 |
| 46 | 5 | NANDROLONE | 0.625 | 300 | 403 | 339 |
| 47 | 0 | NANDROLONE | 0.625 | 100 | 100 | 100 |

Examples 48-75

TWEEN 60 was tested in vivo in chewing gum compositions in the manner described above. The results appear from Table 8.

TABLE 8

| Example No. | TWEEN 60 weight % | Active agent | Content % | Relative Release 2 min. | 5 min. | 10.min |
|---|---|---|---|---|---|---|
| 48 | 5 | PARACETAMOL | 10 | 289 | 240 | 151 |
| 49 | 3 | PARACETAMOL | 10 | 268 | 230 | 149 |
| 50 | 1 | PARACETAMOL | 10 | 116 | 140 | 106 |
| 51 | 0 | PARACETAMOL | 10 | 100 | 100 | 100 |
| 52 | 5 | MENTHOL | 1.3 | 348 | 392 | 188 |
| 53 | 3 | MENTHOL | 1.3 | 226 | 235 | 157 |
| 54 | 1 | MENTHOL | 1.3 | 109 | 146 | 61 |
| 55 | 0 | MENTHOL | 1.3 | 100 | 100 | 100 |
| 56 | 5 | 1.8 CINEOL | 1.0 | 201 | 152 | 107 |
| 57 | 0 | 1.8 CINEOL | 1.0 | 100 | 100 | 100 |
| 58 | 5 | ANETHOL | 0.2 | 202 | 173 | 129 |
| 59 | 0 | ANETHOL | 0.2 | 100 | 100 | 100 |
| 60 | 5 | SODIUM FLUORIDE | 0.075 | 160 | 145 | 125 |
| 61 | 0 | SODIUM FLOURIDE | 0.075 | 100 | 100 | 100 |
| 62 | 5 | CINNARIZINE | 0.625 | U | U | U |
| 63 | 0 | CINNARIZINE | 0.625 | 100 | 100 | 100 |
| 64 | 5 | CYCLIZINE, HCl | 6.25 | 2540 | 775 | 216 |
| 65 | 0 | CYCLIZINE, HCl | 6.25 | 100 | 100 | 100 |
| 66 | 5 | COFFEINE | 4.4 | 300 | 210 | 190 |
| 67 | 3 | COFFEINE | 4.4 | 210 | 190 | 190 |
| 68 | 1 | COFFEINE | 4.4 | 125 | 115 | 160 |
| 69 | 0 | COFFEINE | 4.4 | 100 | 100 | 100 |
| 70 | 5 | NICOTINE | 0.25 | 250 | 210 | 160 |
| 71 | 0 | NICOTINE | 0.25 | 100 | 100 | 100 |
| 72 | 5 | SACCHARIN | 0.1 | U | 370 | 200 |
| 73 | 0 | SACCHARIN | 0.1 | 100 | 100 | 100 |
| 74 | 5 | ASPARTAME | 0.1 | 247 | 141 | 81 |
| 75 | 0 | ASPARTAME | 0.1 | 100 | 100 | 100 |

Examples 76–79

The use of blockcopolymers of ethylene oxide and propyleneoxide, PLURONIC L64, HLB 15, as solubilizer was tested in vitro in the manner described above. The results appear from Table 9.

TABLE 9

| Example No. | PLURONIC L64 weight % | Active agent | Content % | Relative Release 2 min. | 10 min. | 30.min |
|---|---|---|---|---|---|---|
| 76 | 1 | NYSTATIN | 6.25 | 800 | 3000 | 2100 |
| 77 | 0 | NYSTATIN | 6.25 | 100 | 100 | 100 |
| 78 | 5 | MICONAZOLE | 6.25 | U | 62000 | 4500 |
| 79 | 0 | MICONAZOLE | 6.25 | 100 | 100 | 100 |

Examples 80–87

PLURONIC L64 was tasted in vive in chewing gum compositions in the manner described above. The results appear from Table 10.

TABLE 10

| Example No. | PLURONIC L64 weight % | Active agent | Content % | Relative Release 2 min. | 5 min. | 10.min |
|---|---|---|---|---|---|---|
| 80 | 5 | PARACETAMOL | 10 | 525 | 334 | 199 |
| 81 | 0 | PARACETAMOL | 10 | 100 | 100 | 100 |
| 82 | 5 | MENTHOL | 0.9 | 95 | 122 | 149 |
| 83 | 0 | MENTHOL | 0.9 | 100 | 100 | 100 |
| 84 | 5 | 1.8 CINEOL | 1.0 | 76 | 108 | 117 |

TABLE 10-continued

| Example No. | PLURONIC L64 weight % | Active agent | Content % | Relative Release 2 min. | 5 min. | 10.min |
|---|---|---|---|---|---|---|
| 85 | 0 | 1.8 CINEOL | 1.0 | 100 | 100 | 100 |
| 86 | 5 | ANETHOL | 0.2 | 87 | 109 | 95 |
| 87 | 0 | ANETHOL | 0.2 | 100 | 100 | 100 |

Examples 88–91

The use of polyoxyl-40-hydrogenated Castor Oil, CREMOPHOR RH 40, from BASF, HLB 15, as solubilizer was tested in vitro in the manner described above. The results appear from Table 11.

TABLE 11

| Example No. | CREMOPHOR RH 40 weight % | Active agent | Content % | Relative Release 2 min. | 10 min. | 30.min |
|---|---|---|---|---|---|---|
| 88 | 1 | NYSTATIN | 6.25 | 13700 | 15000 | 9400 |
| 89 | 0 | NYSTATIN | 6.25 | 100 | 100 | 100 |
| 90 | 5 | MICONAZOLE | 6.25 | U | U | 4846 |
| 91 | 0 | MICONAZOLE | 6.25 | 100 | 100 | 100 |

Examples 92–99

CREMOPHOR RH 40 was tested in vivo in chewing gum compositions in the manner described above. The results appear from Table 12.

TABLE 12

| Example No. | CREMOPHOR RH 40 weight % | Active agent | Content % | Relative Release 2 min. | 5 min. | 10.min |
|---|---|---|---|---|---|---|
| 92 | 5 | PARACETAMOL | 10 | 555 | 328 | 189 |
| 93 | 0 | PARACETAMOL | 10 | 100 | 100 | 100 |
| 94 | 5 | MENTHOL | 0.9 | 144 | 155 | 123 |
| 95 | 0 | MENTHOL | 0.9 | 100 | 100 | 100 |
| 96 | 5 | 1.8 CINEOL | 1.0 | 156 | 139 | 104 |
| 97 | 0 | 1.8 CINEOL | 1.0 | 100 | 100 | 100 |
| 98 | 5 | ANETHOL | 0.2 | 124 | 120 | 84 |
| 99 | 0 | ANETHOL | 0.2 | 100 | 100 | 100 |

Examples 100–103

The use of polyoxyethylene sorbitan fatty acid ester, TWEEN 20, HLB 16.7, as solubilizer was tested in vitro in the manner described above. The results appear from Table 13.

TABLE 13

| Example No. | TWEEN 20 weight % | Active agent | Content % | Relative Release 2 min. | 10 min. | 30.min |
|---|---|---|---|---|---|---|
| 100 | 1 | NYSTATIN | 6.25 | 16910 | 12450 | 8600 |
| 101 | 0 | NYSTATIN | 6.25 | 100 | 100 | 100 |
| 102 | 5 | MICONAZOLE | 6.25 | U | 128000 | 23550 |
| 103 | 0 | MICONAZOLE | 6.25 | 100 | 100 | 100 |

Examples 104–107

The use of polyoxyethylene (49)-stearate, RS-55-40 from Hefti AG, Zürich, HLB 17.5. as solubilizer was tested in vitro in the manner described above. The results appear from Table 14.

TABLE 14

| Example No. | RS-55-40 weight % | Active agent | Content % | Relative Release 2 min. | 10 min. | 30.min |
|---|---|---|---|---|---|---|
| 104 | 1 | NYSTATIN | 6.25 | 1725 | 7840 | 5460 |
| 105 | 0 | NYSTATIN | 6.25 | 100 | 100 | 100 |
| 106 | 5 | MICONAZOLE | 6.25 | U | 148000 | 27000 |
| 107 | 0 | MICONAZOLE | 6.25 | 100 | 100 | 100 |

Examples 108–111

The use of sodium laurylsulfate as solubilizer was tested in vitro in the manner described above. The results appear from Table 20.

TABLE 20

| Example No. | Na-laur-sulf. weight % | Active agent | Content % | Relative Release 2 min. | 10 min. | 30. min |
|---|---|---|---|---|---|---|
| 108 | 1 | NYSTATIN | 6.25 | 14000 | 18500 | 11300 |
| 109 | 0 | NYSTATIN | 6.25 | 100 | 100 | 100 |
| 110 | 5 | MICON-AZOLE | 6.25 | U | 12000 | 650 |
| 111 | 0 | MICON-AZOLE | 6.25 | 100 | 100 | 100 |

Example 112

The present example illustrates the use of a dispersion of the active agent in a carrier in the chewing gum composition according to the invention.

| Ingredient | Weight % |
|---|---|
| Gum base | 35.8 |
| Hydrogenated glucose syrup | 10.0 |
| Miconazole | 5.6 |
| Solubilizer | 6.6 |
| PEG 6000 | 21.8 |
| Sorbitol | 18.3 |
| Aroma agent | 1.9 |

5.6 g miconazole is mixed with 21.8 g polyethylene glycole 6000. The mixture is heated to 85° C. for 5 to 10 minutes. The melt blend is cooled to 10°–15° C. on aluminum sheets before being ground and sieved to a particle size of approximately 300 um. The powderised solid dispersion is mixed with 6.6 g solubilizer and added to the chewing gum mass.

Chewing gum bits are then prepared as described under general methods.

In the actual example the bits are cut into bits of 900 mg which are subsequently coated with a thin layer of sorbitol with a little flavouring added. The weight of each bit is then 920 mg.

Examples 113–115 and Comparison Example B

Further chewing gum compositions analogous with example 144 are prepared in the manner described above.

Example 113

| Ingredient | Weight % |
|---|---|
| Gum base | 35.8 |
| Hydrogenated glucose syrup | 10.0 |
| Nystatin | 6.25 |
| Tween ™ 60 | 6.25 |
| Sorbitol | 39.8 |
| Aroma agent | 1.9 |

Example 114

| Ingredient | Weight % |
|---|---|
| Gum base | 35.8 |
| Hydrogenated glucose syrup | 10.0 |
| Nystatin | 6.25 |
| Cremophor ™ RH 40 | 6.25 |
| Sorbitol | 39.8 |
| Aroma agent | 1.9 |

Example 115

| Ingredient | Weight % |
|---|---|
| Gum base | 35.8 |
| Hydrogenated glucose syrup | 10.0 |
| Nystatin | 6.25 |
| Panodan ™ AB 90 | 6.25 |
| Sorbitol | 39.8 |
| Aroma agent | 1.9 |

Comparison Example B

| Ingredient | Weight % |
|---|---|
| Gum base | 35.8 |
| Hydrogenated glucose syrup | 10.0 |
| Nystatin | 6.3 |
| Sorbitol | 46.0 |
| Aroma agent | 1.9 |

Test Results from in vitro Test of Chewing Gum Compositions According to the Invention In vitro tests of the preparations according to the examples 113, 114 and 115 and comparison example B were carried out on a chewing machine by chewing 1 chewing gum bit with a weight of 800 mg for 30 minutes. The figures indicate the average value of the three chewings stated as ug nyscatin per ml. phosphate buffer, pH value 7.4.

| Example No. | Time (min.) | | |
|---|---|---|---|
| | 2 | 10 | 30 |
| 113 | 807.7 | 70.6 | 7.0 |
| 114 | 1680.9 | 57.8 | 5.2 |
| 115 | 1917.8 | 44.1 | 2.6 |
| Comparison example B | 6.4 | 5.9 | 3.2 |

Again it is clearly seen than a significant improvement of the rate of release and the quantity released from the compositions according to the invention are obtained compared to the comparison composition.

Example 116

In addition to the basic formulation 1 above a number of further chewing gum formulations have been tested. Tests have thus been carried out with both the same gum base and with other gum bases.

a) Same gum base

At these tests nystatin and paracetamol were used as active agents and TWEEN 60 as solubilizer. The formulations tested differ from the basic formulation 1 in having higher or lower gum base content, the admixture of inorganic filler, the use of other flavourings (fruit, spearmint) and other sweeteners (xylitol, glycerol). In these test the known effect was demonstrated, chat is that a higher base content results in a slower and lesser release, but apart from this, the same improved release pattern as a result of the addition of a solubilizer was seen.

b) Other gum bases

Furthermore, tests have been made wherein the terpene resin in basic formulation 1 has been replaced by others of the essential resins stated in claim 1. Chewing stable chewing gums with the desired accelerated release of the active agent were obtained.

The invention being thus described, it will be obvious that the same may be varied in many ways. Such variations are not to be regarded as deviations from the idea and scope of the inventions and all such modifications as would be obvious to persons skilled in the art, are intended to be included within the scope of the following claims.

Example 145

| Ingredient | Weight % |
|---|---|
| Gum base | 35.8 |
| Hydrogenated glucose syrup | 10.0 |
| Miconazole | 5.5 |
| Lecithin | 6.6 |
| Sorbitol | 40.2 |
| Aroma agent | 1.9 |

The preparation takes place analogous with example 144 apart from the fact that of course no preparation of a solid dispersion takes place.

Comparison Example A

| Ingredient | Weight % |
|---|---|
| Gum base | 35.8 |
| Hydrogenated glucose syrup | 10.0 |
| Miconazole | 5.6 |
| Sorbitol | 46.7 |
| Aroma agent | 1.9 |

Example 146

| Ingredient | Weight % |
|---|---|
| Gum base | 35.8 |
| Hydrogenated glucose syrup | 10.0 |
| Nystatin | 6.25 |
| Tween ™ 60 | 6.25 |
| Sorbitol | 39.8 |
| Aroma agent | 1.9 |

Example 147

| Ingredient | Weight % |
|---|---|
| Gum base | 35.8 |
| Hydrogenated glucose syrup | 10.0 |
| Nystatin | 6.25 |
| Cremophor ™ RH 40 | 6.25 |
| Sorbitol | 39.8 |
| Aroma agent | 1.9 |

Example 148

| Ingredient | Weight % |
|---|---|
| Gum base | 35.8 |
| Hydrogenated glucose syrup | 10.0 |
| Nystatin | 6.25 |
| Panodan ™ AB 90 | 6.25 |
| Sorbitol | 39.8 |
| Aroma agent | 1.9 |

Comparison Example B

| Ingredient | Weight % |
|---|---|
| Gum base | 35.8 |
| Hydrogenated glucose syrup | 10.0 |
| Nystatin | 6.3 |
| Sorbitol | 46.0 |
| Aroma agent | 1.9 |

Test Results from in vitro and in vivo Test of Chewing Gum Compositions According to the Invention The results indicated in Table 22 below are the result of an in vivo test of chewing gum compositiosn according to the examples 144–145 compared to the chewing gum composition according to comparison example A carried out on 6 test persons, measured after chewing of 1 chewing gum bit with a weight of 900 mg for 30 minutes. The figures indicate µg miconazole per ml. of saliva.

TABLE 22

| Example No. | Time (min.) | | | | |
|---|---|---|---|---|---|
| | 2 | 10 | 30 | 60 | 120 |
| 144 | 36.6 | 6.5 | 8.7 | 1.4 | 0.7 |
| 145 | 18.8 | 12.7 | 10.7 | 2.0 | 1.2 |
| Comparison example A | 3.7 | 1.8 | 1.9 | 0.5 | 0.3 |

As appears from the above Table, a clearly increased rate of release and an increase in the quantity released are obtained with the preparations according to the invention compared to the comparison composition.

Furthermore in vitro tests of the preparations according to the examples 146, 147 and 148 and comparison example B were carried out on a chewing machine by chewing 1 chewing gum bit with a weight of 800 mg for 30 minutes. The figures indicate the average value of the three chewings stated as μg nystatin per ml. phosphate buffer, pH value 7.4.

TABLE 23

| Example No. | Time (min.) | | |
|---|---|---|---|
| | 2 | 10 | 30 |
| 146 | 807.7 | 70.6 | 7.0 |
| 147 | 1680.9 | 57.8 | 5.2 |
| 148 | 1917.8 | 44.1 | 2.6 |
| Comparison example B | 6.4 | 5.9 | 3.2 |

Again it is clearly seen that a significant improvement of the rate of release and the quantity released from the compositions according to the invention are obtained compared to the comparison composition.

Example 149

In addition to the basic formulation 1 above a number of further chewing gum formulations have been tested. Tests have thus been carried out with both the same gum base and with other gum bases.

a) Same gum base

At these tests nystatin and paracetamol were used as active agents and TWEEN 60 as solubilizer. The formulations tested differ from the basic formulation 1 in having higher or lower gum base content, the admixture of inorganic filler, the use of other flavourings (fruit, spearmint) and other sweeteners (xylitol, glycerol). In these test the known effect was demonstrated, that is that a higher base content results in a slower and lesser release, but apart from this, the same improved release pattern as a result of the addition of a solubilizer was seen.

b) Other gum bases

Furthermore, tests have been made wherein the terpene resin in basic formulation 1 has been replaced by others of the essential resins stated in claim 1. Chewing stable chewing gums with the desired accelerated release of the active agent were obtained.

The invention being thus described, it will be obvious that the same may be varied in many ways. Such variations are not to be regarded as deviations from the idea and scope of the inventions and all such modifications as would be obvious to persons skilled in the art, are intended to be included within the scope of the following claims.

We claim:

1. Chewing gum composition with accelerated, controlled release of substantially fat-soluble active agents, produced by combining
   i) a chewing gum base having a resin component, wherein said resin component of the chewing gum base comprises at least 25 weight % of a resin selected from the group consisting of terpene resins, glycerol ester of polymerized rosin, pentaerythritol ester of wood or gum rosin, pentaerythritol ester of partially hydrogenated wood or gum rosin, glycerol ester of partially hydrogenated wood or gum rosin, and high molecular weight polyvinyl acetate resins with a molecular weight of at least 30,000, with
   ii) one or more substantially fat-soluble active agents, additives, and at least one solubilizer in a quantity of 1–10 weight %, said solubilizer having an HLB value of 14–20.

2. Chewing gum composition as claimed in claim 1 wherein the resin component of the chewing gum base contains at least 40% of a resin selected from the group consisting of terpene resins, glycerol ester of polymerized rosin, pentaerythritol ester of wood or gum rosin, pentaerythritol ester of partially hydrogenated wood or gum rosin, glycerol ester of partially hydrogenated wood or gum rosin and high molecular weight polyvinyl acetate resins with a molecular weight of at least 30,000.

3. Composition as claimed in claim 1 wherein the resin component of the chewing gum base contains a terpene resin of natural or synthetic origin.

4. Composition as claimed in claim 1 wherein the solubilizer of the composition is selected from the group consisting of lecithin, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerolesters of internal esterified castor oil acid, sodium stearoyllactylate, sodium lauryl sulfate, sorbitan esters of fatty acids, polyoxyethylated hydrogenated castor oil, blockcopolymers of ethylene oxide and propylene oxide, polyoxyethylene fatty alcohol ether, sorbitan ester of fatty acid and polyoxyethylene steraric acid ester.

5. Chewing gum composition as claimed in claim 4 wherein the solubilizer is selected from the group consisting of polyoxyethylene stearate, polyoxyethylene sorbitan fatty acid ester, mono and diacetyl tartaric acid esters of mono and diglycerides of edible fatty acids, citric acid ester of mono and diglycerides of edible fatty acids, sodium stearoyllactylate, sodium laurylsulfate, polyoxyethylated hydrogenated castor oil, blockcopolymers of ethylene oxide and propylene oxide and polyoxyethylene fatty alcohol ether.

6. Chewing gum composition as claimed in claim 1 wherein 3–6 weight % solubilizer is added to the chewing gum composition.

7. Chewing gum composition as claimed in claim 1 wherein the composition further contains up to 60 weight % of at least one carrier, which carrier forms a solid dispersion together with the active agent.

8. Composition as claimed in claim 7 wherein the carrier is selected from the group consisting of polyethylene glycol and polyvinyl pyrrolidone.

9. Composition as claimed in claim 8 wherein the carrier is polyethyleneglycol 1000–20,000.

10. Composition as claimed in claim 1 wherein the active agent has a water-solubility of less than 10 g/100 ml.

11. Chewing gum composition as claimed in claim 10 wherein the active agent is selected from the group consisting of dietary supplement, oral and dental compositions, antiseptics, pH adjusting agents, anti-smoking agents, sweeteners, flavorings, aroma agents and medicines.

12. Chewing gum composition as claimed in claim 11 wherein the active agent is selected from the group consisting of paracetamol, benzocaine, cinnarizine, menthol, carvone, coffeine, chlorhexidine-diacetate, cyclizine hydrochloride, 1,8-cineol, nandrolone, miconazole, nystatin, aspartame, sodium fluoride, nicotine, saccharin, cetylpyridinium chloride, other quaternary ammonium-compounds, vitamin E, vitamin A, vitamin D, glibenclamide or derivatives thereof, progesterone, acetylsalicylic acid, dimenhydrinate, cyclizine, metronidazole, sodium hydrogencarbonate, the active components from ginkgo, the active components from propolis, the active components from ginseng, methadone, oil of peppermint, salicylamide, hydrocortisone and astemizole.

13. Process for the preparation of a chewing gum composition as claimed in claim 1 comprising the steps of preparing a chewing gum base on the basis of conventional chewing gum base ingredients including a resin portion, wherein the resin portion comprises at least 25 weight % of a resin selected from the group consisting of terpene resins, glycerol ester of polymerized rosin, pentaerythritol ester of polymerized rosin, pentaerythritol ester of wood or gum rosin, pentaerythritol ester of partially hydrogenated wood or gum rosin, glycerol ester of partially hydrogenated wood or gum rosin and high molecular weight polyvinyl acetate resins with a molecular weight of at least 30,000, and then preparing a chewing gum composition while adding at least one substantially fat-soluble active agent and 1–10 weight % of at least one solubilizer, said solubilizer having an HLB value of 14–20.

14. Process as claimed in claim 13 comprising the further step of mixing the active agent intimately with the solubilizer to form a mixture and then admixing the mixture to the chewing gum composition.

15. Process as claimed in claim 14 comprising the further step of forming a solid dispersion of the active agent in a carrier prior to mixing the active agent with the solubilizer.

16. Process for making a chewing gum composition, comprising the step of combining a solubilizer for accelerated, controlled release of substantially fat-soluble active agents with a composition comprising a chewing gum base having a resin component comprising at least 25 weight % of a resin selected from the group consisting of terpene resins, glycerol ester of polymerized rosin, pentaerythritol ester of wood or gum rosin, pentaerythritol ester of partially hydrogenated wood or gum rosin, glycerol ester of partially hydrogenated wood or gum rosin and high molecular weight polyvinyl acetate resins with a molecular weight of at least 30,000, said solubilizer being present in a quantity of 1–10 weight % of said chewing gum composition and having an HLB value of 14–20.

* * * * *